United States Patent
Bodmer

[19]

[11] Patent Number: 5,843,010
[45] Date of Patent: Dec. 1, 1998

[54] HEEL AND ANKLE APPLIANCE

[76] Inventor: E. James Bodmer, 2135 E. Calle Maderas, Mesa, Ariz. 85213

[21] Appl. No.: 593,287

[22] Filed: Jan. 29, 1996

[51] Int. Cl.$^6$ ........................................................ A61F 5/00
[52] U.S. Cl. .................................. 602/27; 602/5; 602/23; 602/65; 128/882
[58] Field of Search ............................... 602/4, 5, 20, 21, 602/23, 24, 26, 27, 28, 29, 60, 61, 62, 63, 64, 65, 66; 128/877, 878, 879, 881, 882

[56] References Cited

U.S. PATENT DOCUMENTS

| | | |
|---|---|---|
| 2,557,603 | 6/1951 | Invidiato . |
| 3,827,430 | 8/1974 | Fadden . |
| 3,916,886 | 11/1975 | Rogers . |
| 3,976,059 | 8/1976 | Lonardo . |
| 4,294,238 | 10/1981 | Woodford . |
| 4,497,070 | 2/1985 | Cho . |
| 5,020,523 | 6/1991 | Bodine . |
| 5,088,480 | 2/1992 | Wang . |
| 5,176,623 | 1/1993 | Stetman et al. ............................ 602/27 |
| 5,197,942 | 3/1993 | Brady . |
| 5,298,013 | 3/1994 | Lonardo . |
| 5,431,624 | 7/1995 | Saxton et al. . |
| 5,605,535 | 2/1997 | Lepage ...................................... 602/27 |

*Primary Examiner*—Richard J. Apley
*Assistant Examiner*—Kim M. Lee
*Attorney, Agent, or Firm*—John D. Lister

[57] ABSTRACT

An appliance for protecting, supporting and cushioning the heel and ankle, to facilitate the recuperation, rehabilitation or other healing of the heel and/or ankle from medical procedures, injuries or other disorders, includes a pliable cupping component which receives and is adjustably secured to the heel portion of the foot and the ankle. The fastening means for securing the cupping component to the heel and ankle provides support for the tendons and tendon sheaths in the heel and ankle. A pair of selectively adjustable support straps extend from the sides of the cupping component to an upper fastening means immediately below the knee. The support straps exert an upward and supportive force on the heel portion of the foot and limit the flexing of the ankle joint without exerting an upward force on the apophysis or growth center of the calcaneus bone which is located at the posterior portion of the calcaneus bone adjacent and below the attachment of the achilles tendon to this bone.

6 Claims, 2 Drawing Sheets

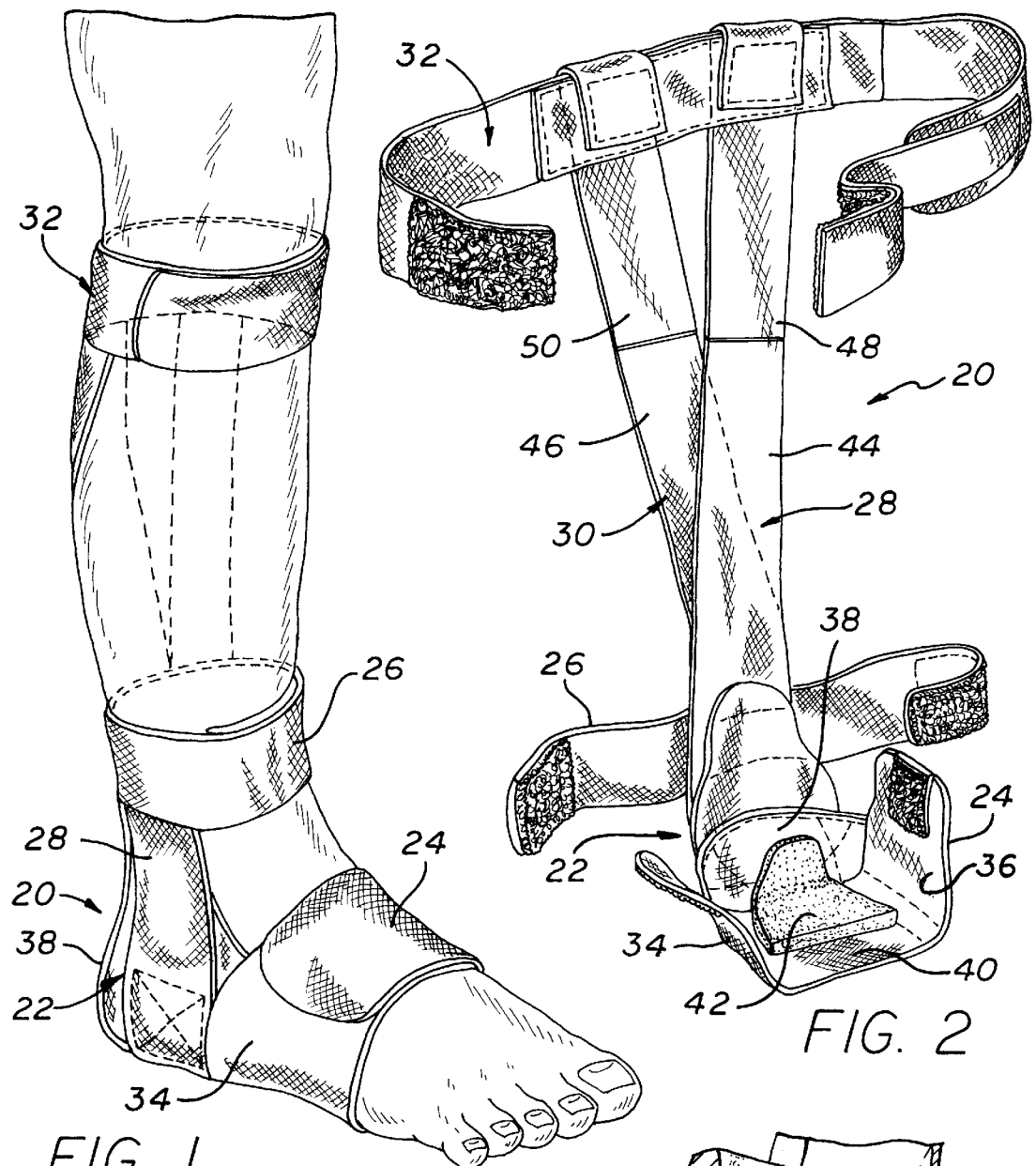
FIG. 1
FIG. 2
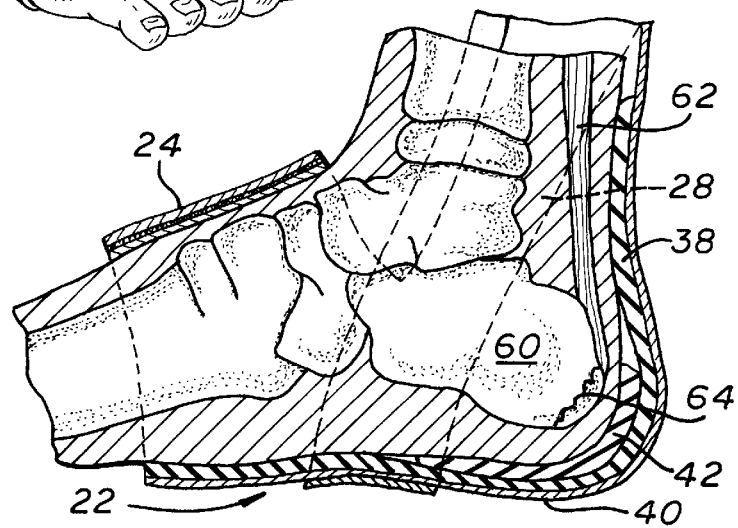
FIG. 3

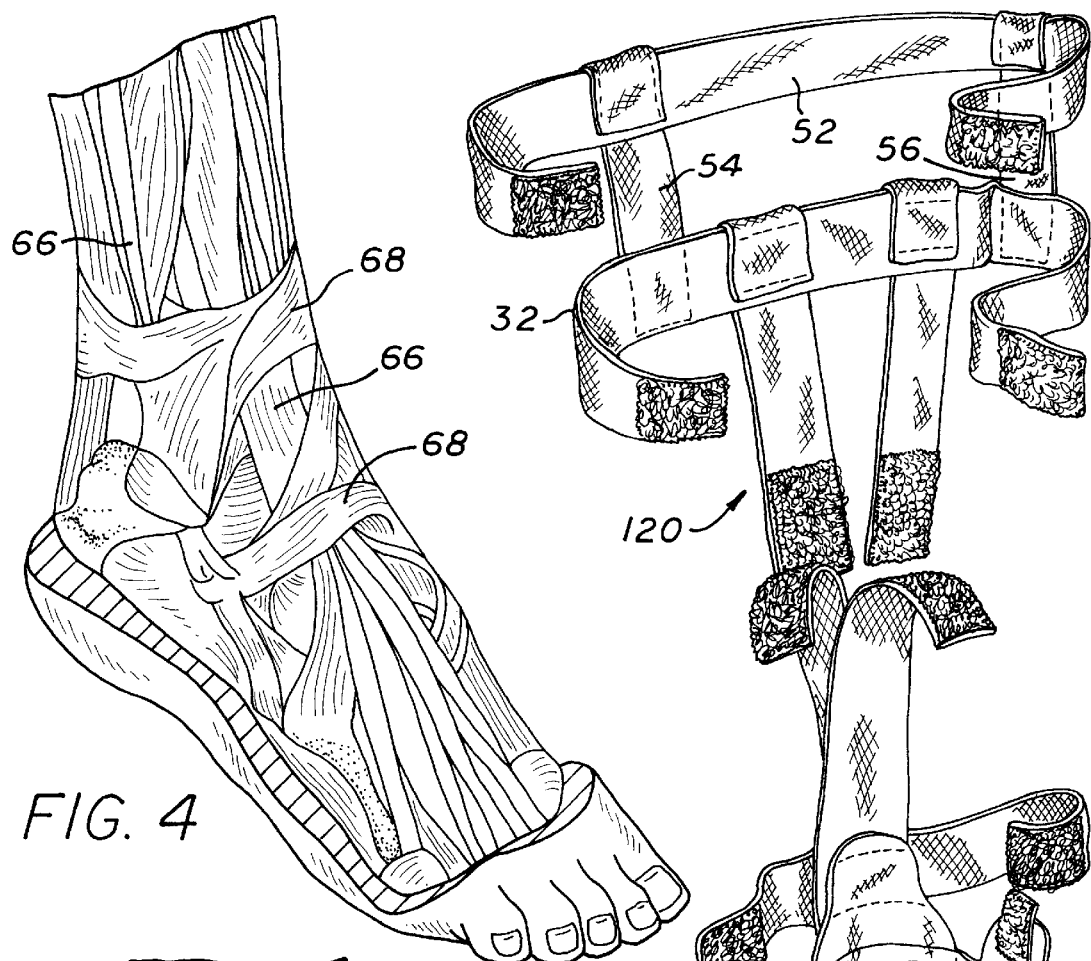
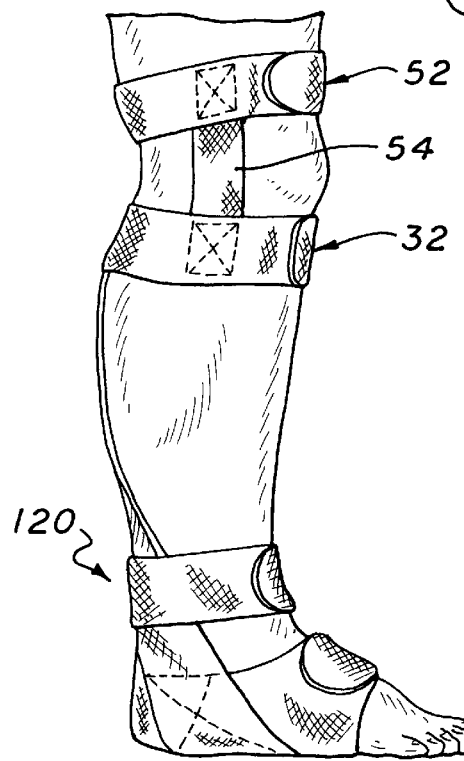

HEEL AND ANKLE APPLIANCE

BACKGROUND OF THE INVENTION

The present invention relates to a heel and ankle appliance and, in particular, to a heel and ankle appliance that can be custom fitted to the patient; can be easily applied and removed by the patient or physician; permits patient mobility; and is especially designed to provide protection, indirect support and cushioning for the back portion of the heel bone and the point of attachment of the achilles tendon to this bone.

When a patient's heel and/or ankle is healing from an injury such as: achilles tendonitis; a heel fracture or a heel spur; apophysitis (a disturbance in the growth center of the heel bone); an injury to the tendons and/or tendon sheaths located in the front of the ankle and/or upper portion of the foot; a medical procedure; or other physical disorders or diseases of the heel and/or ankle, the patient's ankle is normally immobilized by rigid splints or casts and the patient must forgo or greatly curtail any normal weight bearing activities such as standing and walking. In addition to permitting only limited mobility, rigid splints and casts typically cause the patient discomfort; can remain in place on the patient for relatively long periods of time during the patient's recuperation and contribute to atrophy of the lower leg muscles; and can cause sores or rashes to develop on the leg, ankle and foot of the patient due to chaffing and a lack of air to the areas enclosed or covered by the rigid splint or cast.

With injuries such as achilles tendonitis, certain heel fractures and spurs, and a physical disorder such as apophysitis, it is particularly important to protect the rear portion of the heel bone and the point of attachment of the achilles tendon to the rear of the heel bone from impacts and other stresses which can traumatize the rear portion of the heel bone and/or the attachment of the achilles tendon to the heel bone and thereby cause further injury or at least prolong the recuperation or rehabilitation period for the injury or disorder.

U.S. Pat. No. 4,294,238; inventor Woodford; issued Oct. 13, 1981; discloses a lower limb muscle aid device for assisting and relaxing a user's leg muscles. The device can be applied to and removed from the user's leg and foot and permits mobility. However, the device is not an appliance for use in the recuperation or rehabilitation of heel and ankle disorders, provides no support about the ankle of the user, and does not protect the heel and ankle from being traumatized. In fact, an elastic strap 16 of the Woodford device extends from the sole of the device directly over the rear of the user's heel and could traumatize and further exacerbate certain heel disorders such as apophysitis.

Thus, there has been a need to provide an appliance that: facilitates the recuperation or rehabilitation of heel and ankle injuries and disorders, cushions and protects the patient's heel and ankle from stress and trauma, allows the patient to retain his/her mobility, can be custom fitted to the patient and adjusted as the patient's condition changes for comfort and support, can be easily applied and removed, and is inexpensive. Furthermore, there has been a need for such an appliance which can provide indirect support for the rear portion of the heel bone and the point of attachment of the achilles tendon to the upper rear portion of the heel bone and limit the flexing of the ankle joint to prevent the traumatization of the rear portion of the heel bone and the point of attachment of the achilles tendon to the heel bone due to excessive flexing of the ankle joint during weight bearing activities such as standing and walking.

SUMMARY OF THE INVENTION

The present invention provides an appliance for protecting, supporting and cushioning the heel and ankle of a patient during weight bearing activities, such as walking or standing, to facilitate the recuperation, rehabilitation or other healing of the heel and/or ankle from medical procedures, injuries or other physical disorders. The heel and ankle appliance of the present invention permits the flexing of the ankle joint so that the patient can easily stand and walk and retain his/her mobility without traumatizing the rear portion of the patient's heel bone or the attachment point of the achilles tendon to the upper portion of the heel bone. In addition to permitting the patient to retain his/her mobility, the appliance permits the continued use by the patient of the muscle groups of the lower leg to prevent or at least minimize muscle atrophy of these muscle groups during the patient's recuperation or rehabilitation.

The heel and ankle appliance of the present invention can be selectively adjusted to custom fit the appliance to the patient's lower leg, ankle and foot; is light weight and flexible; can be easily applied; and can be easily removed for the comfort and convenience of the patient when the patient is going to be off of his/her feet such as when sleeping or bathing. The ability to easily apply the appliance to and remove the appliance from the lower limbs of the patient prevents the formation of sores which might otherwise be caused by the extended wear of the appliance, alleviates chaffing of the patient's lower leg, ankle and foot, and also allows air to reach injured areas when the patient is not walking or standing, to facilitate the healing of such areas.

The heel and ankle appliance of the present invention includes a pliable, preferably cushioned, cupping component which receives the heel portion of the patient's foot and the patient's ankle. The cupping component is secured to the heel portion of the foot and the ankle by selectively adjustable fastening straps which permit the cupping component to be custom fitted to the patient's foot and ankle. The fastening straps can be easily fastened to secure the cupping component to the heel portion of the patient's foot and the patient's ankle and easily unfastened, when desired, to remove the heel and ankle appliance from the rear portion of the patient's foot and the patient's ankle. Thus, the heel and ankle appliance of the present invention can be repeatedly applied to and removed from the patient's foot and ankle as needed for sleeping, bathing, treatment, adjustments, bandage changes, etc. In addition to securing the cupping component to the patient's foot and ankle, the fastening straps can also provide support for certain tendons and tendon sheaths located in the foot and ankle of the patient.

The heel and ankle appliance of the present invention also includes a pair of selectively adjustable support straps which extend from the sides of the cupping component to an adjustable fastening strap located immediately below the knee of the patient. This upper fastening strap can be selectively adjusted to fit the patient and repeatedly fastened and unfastened, as needed, to apply and remove the heel and ankle appliance. The lengths of the support straps can be selectively adjusted to exert an upward supportive force on the heel portion of the patient's foot when the patient's ankle is flexed a predetermined extent to provide support for the heel and limit the flexing of the patient's ankle joint to prevent the traumatization of the rear portion of the heel bone and the point of attachment of the achilles tendon to the heel bone when the patient is engaged in a weight bearing activity such as standing or walking. By securing the support straps to the cupping component forward of the rear portion of the heel bone and on the sides of the heel, the upward force exerted by the support straps on the heel does not exert an upward force directly on the back portion of the heel, at the posterior bottom portion of the calcaneus (heel) bone, adjacent and below the point of attachment of the achilles tendon to this bone.

BRIEF DESCRIPTION OF THE DRAWINGS

FIG. 1 is a perspective view of a first embodiment of the heel and ankle appliance of the present invention applied to a patient's lower leg and foot.

FIG. 2 is a perspective view of the first embodiment of the heel and ankle appliance of the present invention.

FIG. 3 is a side sectional view of the heel portion of a foot showing the basic bone and tendon structure of the heel and the cupping component of the heel and ankle appliance of the present invention in place on the heel portion of the foot.

FIG. 4 is a perspective view of a foot and ankle showing certain of the major tendons and tendon sheaths which can be protected, supported and cushioned with the heel and ankle appliance of the present invention.

FIG. 5 is a perspective view of a second embodiment of the heel and ankle appliance of the present invention.

FIG. 6 is a side view of the second embodiment of the heel and ankle appliance of the present invention applied to a patient's leg and foot.

DESCRIPTION OF THE PREFERRED EMBODIMENTS

FIG. 1 shows one embodiment 20 of the heel and ankle appliance of the present invention applied to the lower leg and foot of a patient. The heel and ankle appliance includes a cupping component 22; foot and ankle fasteners 24 and 26 for securing the cupping component 22 to the heel portion of the foot and the ankle of the patient, respectively; support straps 28 and 30 supporting the heel portion of the foot through the cupping component 22; and an upper fastener 32 for securing the support straps 28 and 30 to the leg of the patient below the knee and above the calf of the patient.

The cupping component 22 is made of a pliable material, e.g. a pliable, resilient foam encased within a cloth envelope or a similar cushioning material, and encloses the sides, rear and sole of the heel portion of the patient's foot as well as the sides and rear of the patient's ankle. The foot and ankle fasteners 24 and 26 encircle the upper surface of the heel portion of the patient's foot and the patient's ankle.

As shown in FIGS. 1–3, the pliable cupping component includes side portions 34 and 36 which enclose and cushion the sides of the heel portion of the patient's foot; a rear portion 38 which encloses and cushions the back of the heel portion of the patient's foot and the back of the patient's ankle; and a sole portion 40 which encloses and cushions the sole of the heel portion of the patient's foot. The heel is a poorly vascularized area of the body which generally prolongs the healing period for sores and other such injuries to this portion of the body. Accordingly, to provide additional protection for this area during the patient's recuperation or rehabilitation, an additional pad 42 of a pliable, resilient foam or other similar cushioning material is preferably provided on the sole portion 40 of the cupping component. As shown in FIG. 3, the pad 42 can be extended upward into the rear portion 38 of the cupping component 22 to provide additional protection and cushioning for the rear portion of the heel bone and the attachment point of the achilles tendon to the heel bone.

The foot and ankle fasteners 24 and 26 can be readily fastened and unfastened, when desired, and are selectively adjustable so that the pliable cupping component 22 of the heel and ankle appliance 20 of the present invention can be easily applied and secured to or removed from the foot and ankle of the patient and custom fitted to the foot and ankle of the patient. Preferably, the foot and ankle fasteners 24 and 26 each include opposed, overlapping pliable fastening straps which are secured together, in the overlapped position by a self-holding material, such as a VELCRO material, when the heel and ankle appliance is being worn. The self-holding material used to secure the overlapping portions of the fastening straps 24 and 26 together permits the fastening straps to be easily fastened about the patient when the heel and ankle appliance 20 is being applied and easily unfastened from the patient when the heel and ankle appliance 20 is being removed from the patient. By changing the degree of overlap of the opposed fastening straps the heel appliance can be selectively adjusted to fit the foot and ankle of the patient. Thus, the heel and ankle appliance 20 of the present invention can be comfortably worn by the patient; adjusted to properly fit the patient during the patient's recuperation or rehabilitation, such as when swelling due to an injury subsides; easily and quickly removed by the patient for sleeping or bathing; and easily and quickly reapplied by the patient before the patient engages in a weight bearing activity such as standing or walking. While pliable fastening straps which can be repeatedly fastened and unfastened and adjustably secured together in their overlapped position by a self holding material, such as a VELCRO material, are preferred, other means for fastening and adjustably securing the foot and ankle fastening straps together may be used.

As shown best in FIG. 1 and FIG. 3 in phantom line, the support straps 28 and 30 are secured by stitching or other conventional means to the side portions 34 and 36 of the cupping component 22 forward of the rear portion 38 of the cupping component so that the support straps 34 and 36 do not exert pressure directly on the rear of the heel bone or the attachment of the achilles tendon to the heel bone. Preferably, the support straps 28 and 30 are made of an inextensible or substantially inextensible, pliable conventional strapping material which can be enveloped within a cushioning material, such as cloth covered resilient foam, for the comfort of the patient.

The support straps 28 and 30 can be one continuous strap that passes under the sole portion 40 of the cupping component 22 or the support straps can be separate straps which are secured to the side portions of the cupping component without passing under the sole portion of the cupping component. The support straps extend from the sides of the cupping component 22 to the upper fastener 32 that encircles the leg of the patient between the knee and the calf. As shown the support straps 28 and 30 crisscross intermediate the cupping component 22 and the upper fastener 32, preferably, at the upper portion of the ankle or immediately above the ankle at the base of the calf. The crisscrossing of the support straps 28 and 30 in this region of the lower leg provides a more anatomically appropriate support for the achilles tendon in this region of the lower leg.

Preferably, the support straps 28 and 30 each have lower portions 44 and 46 which are secured to the cupping component 22 and upper portions 48 and 50 which are secured by stitching or other conventional means to the upper fastener 32. The upper and lower portions of each support strap overlap and are adjustably secured together so that the length of the support straps can be adjusted to a selected length to properly fit the patient. Preferably, the upper and lower portions of the support straps 28 and 30 are secured together in the overlapped position by a self-holding material, such as a VELCRO material, which permits the upper and lower portions of the support straps to be fastened together and unfastened during the repeated use of and adjustments to the heel and ankle appliance 20. By changing the degree of the overlap between the upper and lower portions of the support straps 28 and 30 the lengths of the support straps 28 and 30 can be quickly and easily adjusted to the desired length.

Preferably, the upper fastener 32 comprises a fastening strap with opposed, overlapping pliable end portions which are secured together in the overlapped position by a self-holding material, such as a VELCRO material, which can be repeated fastened together and unfastened. By selectively changing the degree of overlap of the opposed ends of the fastening strap, the upper fastener 32 can be adjusted to fit snugly around the leg of the patient between the knee and the calf. As with the foot and ankle fasteners 24 and 26, the upper fastener 32 permits the heel and ankle appliance 20 of the present invention to be comfortably worn by the patient and to be quickly and easily removed or applied by the patient. Since the upper fastener 32 can be adjusted to snugly fit about the leg of the patient between the knee and the calf, the upper fastener 32 firmly anchors the upper portion of the heel and ankle appliance 20 in place to provide the necessary support to the heel portion of the patient's foot through the support straps 28 and 30 and the cupping component 22. For the added comfort of the patient, the upper fastener 32 can be encased in a cushioning material such as a cotton cloth covered resilient foam.

FIGS. 5 and 6 show a second embodiment 120 of the heel and ankle appliance of the present invention with the VELCRO material of the upper and lower portions of the support straps peeled back. Except for a second, upper leg fastener 52, which is connected to the upper fastener 32 by side straps 54 and 56, the heel and ankle appliance 120 of FIGS. 5 and 6 is identical to the heel and ankle appliance of FIGS. 1–3 and the description of the lower portion of the heel and ankle appliance of the present invention will not be repeated. The second, upper leg fastener 52 comprises a fastening strap with opposed, overlapping pliable end portions which preferably, are secured together in the overlapped position by a self holding material, such as a VELCRO material, which permits the fastener 52 to be repeatedly fastened and unfastened. By selectively changing the degree of overlap of the opposed ends of the fastening strap, the upper leg fastener 52 can be adjusted to fit snugly around the leg of the patient immediately above the knee to further anchor the upper portion of the heel appliance 120 about the leg of the patient. The side straps 54 and 56, which connect the upper leg fastener 52 to the upper fastener 32, are inextensible or substantially inextensible and extend between the fasteners 52 and 32 along the sides of the leg as shown in FIG. 6 so that the straps 54 and 56 do not bind behind the knee when the patient bends his/her leg at the knee and cause discomfort. As with the other fasteners, the upper leg fastener 52 permits the heel appliance 120 to be comfortably worn by the patient and to be quickly and easily removed from or applied to the leg and foot of the patient. As with the other fasteners 24, 26 and 32, the upper leg fastener 52 is preferably encased within a cushioning material for the comfort of the patient and to prevent chaffing of the patient's leg which could cause sores and infections to develop.

FIG. 3 shows the heel portion of a foot with the apophysis or heel bone 60 and the calcaneal or achilles tendon 62 attached to an upper, rear portion of the bone. Among other injuries to or disorders of the heel, direct trauma from the impacts associated with weight bearing activities, such as running, and the pull of the achilles tendon on the upper rear portion of the heel bone can cause repetitive traumatic disturbances to the growth center of the heel bone in children during the development period of that bone in a disorder called apophysitis. This disorder is represented by an irregular appearance 64 in the growth center (apophysis) of the heel bone 60 shown in FIG. 3. Patient's with this condition experience heel pain and local tenderness in the area of the growth center. To relieve the pain and permit the heel bone to mend, the rear portion of the heel bone 60 and the point of attachment of the achilles tendon 62 to the heel bone must be cushioned and protected from impact. In addition, the flexing of the ankle joint beyond a certain degree must be prevented to keep the achilles tendon 62 from pulling on the heel bone at its attachment point to further aggravate the disorder without applying a force on the diseased or injured area.

As shown in FIGS. 2, 3 and 5, the cupping component 22 of the heel and ankle appliance 20 or 120, is preferably made with a cushioning material (e.g. a compressible, resilient cloth covered foam) which overlays or encloses the sole portion of heel, the sides of the heel, and the rear of the heel and ankle to protect the heel and achilles tendon from impacts. In addition, the support straps 28 and 30 of the heel and ankle appliance 20 or 120 provide support to the heel portion of the foot when the ankle is flexed a predetermined degree and limit the degree that the ankle can be flexed to prevent the achilles tendon 62 from pulling on the heel bone 60 with too much force. By selectively adjusting the lengths of the support straps 28 and 30, the degree that the ankle can be flexed and the force that the achilles tendon can apply to the heel bone 60 can be controlled or substantially eliminated. As shown in FIGS. 1, 3 and 6, the support straps 28 and 30 are secured to the sides of the cupping component 22 forward of the rear of the heel bone and do not pass around or over the rear of the heel bone. Thus, the support provided to the heel by the heel and ankle appliance 20 or 120, through the straps 28 and 30 and the cupping component 22, does not exert pressure on the rear of the heel bone to aggravate the heel's growth center or any inflammation present in this area of the heel.

As shown in FIG. 4, tendons 66 and tendon sheaths 68 are located in the front of the ankle and the upper portion of the foot. These tendons 66 and tendon sheaths 68 can be injured or torn and require support and cushioning to facilitate the healing or mending of this tissue. As shown in FIGS. 1, 3 and 6, the foot and ankle fastening straps 24 and 26 can provide the necessary support and cushioning to minimize the stress placed on these tendons during weight bearing activities and facilitate the healing of these tendons and/or tendon sheaths while allowing the patient to be mobile.

In describing the invention, certain embodiments have been used to illustrate the invention and the practices thereof. However, the invention is not limited to these specific embodiments as other embodiments and modifications within the spirit of the invention will readily occur to those skilled in the art on reading this specification. Thus, the invention is not intended to be limited to the specific embodiments disclosed, but is to be limited only by the claims appended hereto.

What is claimed is:

1. A flexible heel and ankle protecting, supporting and cushioning appliance, comprising:

a pliable cupping means for receiving a heel portion of a patient's foot and a patient's ankle comprising, a sole portion for engaging the heel portion of a sole of the foot, first and second side portions for engaging sides of the heel of the foot, a back portion for engaging a back of the heel and the ankle from the sole of the foot to an upper portion of the ankle;

first selectively adjustable fastening means, which can be repeatedly fastened and unfastened and passes over an upper surface of the heel portion of the foot between said first and second side portions of said pliable cupping means, for securing said pliable cupping means to the heel portion of the foot and providing support for tendons and tendon sheaths located beneath the upper surface of the heel portion of the foot;

second selectively adjustable fastening means extending from said back portion of said pliable cupping means, which can be repeatedly fastened and unfastened and encircles the ankle, for securing said pliable cupping means to the ankle and for providing support for tendons and tendon sheaths located in the ankle;

a third selectively adjustable fastening means, which can be repeatedly fastened and unfastened and encircles a leg of the patient between a knee and a calf portion of the leg;

first and second substantially inextensible support straps, secured to and extending from said first and second side portions of said pliable cupping means to said third selectively adjustable fastening means, for exerting an upward force on said pliable cupping means at said first and second side portions of said pliable cupping means to limit the degree that an ankle joint of the patient can be flexed without exerting an upward force on a back portion of the heel of the patient; said first and second support straps crisscrossing each other intermediate said first and second side portions of said pliable cupping means and said third selectively, adjustable fastening means in a region of the lower leg at the rear of the leg to provide support for the achilles tendon in this region of the lower leg.

2. The appliance of claim 1, wherein: said first and second support straps include means for selectively adjusting said first and second support straps in length to permit said appliance to be fitted to the patient and limit the degree that the ankle joint can be flexed.

3. The appliance of claim 2, wherein: said sole portion and said back portion of said pliable cupping means include cushioning means.

4. The appliance of claim 1, wherein: said sole portion and said back portion of said pliable cupping means include cushioning means.

5. The appliance of claim 1, wherein: said pliable cupping means does not include a rigid shell.

6. The appliance of claim 5, wherein: said first and second support straps include means for selectively adjusting said first and second support straps in length to permit said appliance to be fitted to the patient and limit the degree that the ankle joint can be flexed.

* * * * *